(12) United States Patent
Kloke et al.

(10) Patent No.: US 11,993,767 B2
(45) Date of Patent: May 28, 2024

(54) METHOD FOR PRODUCING 3D, BIOCOMPATIBLE POLYMER SCAFFOLD WITH A CELL-FILLED CAVITY

(71) Applicant: CELLBRICKS GmbH, Berlin (DE)

(72) Inventors: Lutz Kloke, Berlin (DE); Alexander Thomas, Berlin (DE); Tobias Lam, Berlin (DE)

(73) Assignee: CELLBRICKS GmbH, Berlin (DE)

( * ) Notice: Subject to any disclaimer, the term of this patent is extended or adjusted under 35 U.S.C. 154(b) by 0 days.

(21) Appl. No.: 17/779,100

(22) PCT Filed: Nov. 20, 2020

(86) PCT No.: PCT/DE2020/100986
§ 371 (c)(1),
(2) Date: Nov. 18, 2022

(87) PCT Pub. No.: WO2021/104571
PCT Pub. Date: Jun. 3, 2021

(65) Prior Publication Data
US 2023/0133963 A1    May 4, 2023

(30) Foreign Application Priority Data
Nov. 27, 2019  (DE) .......................... 102019132214.6

(51) Int. Cl.
| | | |
|---|---|---|
| *C12M 1/12* | (2006.01) | |
| *B29C 64/124* | (2017.01) | |
| *B33Y 10/00* | (2015.01) | |
| *B33Y 70/00* | (2020.01) | |
| *B33Y 80/00* | (2015.01) | |
| *C12N 5/00* | (2006.01) | |

(52) U.S. Cl.
CPC ........... *C12M 25/14* (2013.01); *B29C 64/124* (2017.08); *B33Y 10/00* (2014.12); *B33Y 70/00* (2014.12); *B33Y 80/00* (2014.12); *C12N 5/0068* (2013.01); *C12N 2513/00* (2013.01); *C12N 2537/10* (2013.01)

(58) Field of Classification Search
None
See application file for complete search history.

(56) References Cited

U.S. PATENT DOCUMENTS

| | | |
|---|---|---|
| 2003/0175410 A1 | 9/2003 | Campbell |
| 2019/0040359 A1 | 2/2019 | Nakayama |
| 2021/0107212 A1 | 4/2021 | Kloke |

FOREIGN PATENT DOCUMENTS

| | | | |
|---|---|---|---|
| CN | 101679948 A | 3/2010 | |
| CN | 101883842 A | 11/2010 | |
| CN | 102292113 A | 12/2011 | |
| CN | 107058098 A | 8/2017 | |
| CN | 107148302 A | 9/2017 | |
| EP | 3018531 A1 | 5/2016 | |
| JP | 2017536113 A | 12/2017 | |
| WO | 2005095581 A1 | 10/2005 | |
| WO | 2009042671 A1 | 4/2009 | |
| WO | 2009048435 A1 | 4/2009 | |
| WO | WO-2009042671 A1 * | 4/2009 | ........ B01L 3/502707 |
| WO | 2011038373 A2 | 3/2011 | |
| WO | 2019185508 A1 | 10/2019 | |
| WO | 2019219605 A1 | 11/2019 | |

OTHER PUBLICATIONS

Husar et al. "Photopolymerization-based additive manufacturing for the development of 3D porous scaffolds" (2014), Biomaterials for Bone Regeneration in Novel Techniques and Applications, pp. 149-201 (Year: 2014).*
Ghosh et al. "Addressing Unmet Clinical Needs with 3D Printing Technologies" (2018), Adv Heathcare Mats, vol. 7, No. 1800417: 1-24. (Year: 2018).*
Zhao et al. "Three-dimensional printing of Hela cells for cervical tumor model in vitro" (2014), Biofabrication, vol. 6, No. 035001: 1-10. (Year: 2014).*
English translation of Office Action dated Aug. 3, 2023 in Chinese Patent Application 202080082748.4.
Grix T, Ruppelt A, Thomas A, Amler AK, Noichl BP, Lauster R, Kloke L., Bioprinting Perfusion-Enabled Liver Equivalents for Advanced Organ-on-a-Chip Applications. Genes (Basel). Mar. 22, 2018;9(4):176.
Haemobrick Seeding Protocol, Cellbricks GmbH, Jun. 29, 2020.
Kuo AP, Bhattacharjee N, Lee YS, Castro K, Kim YT, Folch A., High-Precision Stereolithography of Biomicrofluidic Devices. Adv Mater Technol. 2019.
Xia C, Fang NX. 3D microfabricated bioreactor with capillaries. Biomed Microdevices. Dec. 2009.
Japanese Office action dated Nov. 15, 2022, in Japanese patent application No. 2022-530944.
Zhang Rujing: "Stereolithographic hydrogel printing of 3D microfluidic cell culture chips—PHD Thesis", DTU Nanotech, Oct. 1, 2017 (Oct. 1, 2017), XP055775960, URL:http://orbit.dtu.dk/files/142686115/Untitled.pdf.
Zhang Rujing et al: "Stereolithographic hydrogel printing of 3D culture chips with biofunctionalized complex 3D perfusion networks", Lab On a Chip, vol. 17, No. 24, Jan. 1, 2017 (Jan. 1, 2017), pp. 4273-4282.
Thomas Alexander et al: "Vascular bioprinting with enzymatically degradable bioinks via multi-material projection-based stereolithography", Acta Biomaterialia, vol. 117, Sep. 24, 2020 (Sep. 24, 2020), pp. 121-132.

* cited by examiner

*Primary Examiner* — Teresa E Knight
(74) *Attorney, Agent, or Firm* — The Culbertson Group, P.C.

(57) ABSTRACT

A 3D scaffold of a biocompatible polymer and colonized with biological cells is provided. The biological cells can be cultured to form a 3D cell culture construct that closely approximates a physiological architecture. A method for producing the 3D scaffold colonized with biological cells is also provided.

17 Claims, 3 Drawing Sheets

METHOD FOR PRODUCING 3D, BIOCOMPATIBLE POLYMER SCAFFOLD WITH A CELL-FILLED CAVITY

TECHNICAL FIELD OF THE INVENTION

The present invention relates to a 3D scaffold of a biocompatible polymer being colonized with biological cells, in which scaffold the biological cells can be cultured to form a 3D cell culture construct that closely approximates a physiological architecture. Furthermore, the present invention also relates to a method for producing the 3D scaffold colonized with biological cells.

BACKGROUND OF THE INVENTION

Currently, there are only a few possibilities for producing 3D cell cultures in a targeted form. The only possibilities to date are the production of spheroids or microfluidic platforms, or the casting of a gel with cells suspended therein. In contrast, methods according to the invention for the first time gives the possibility of culturing biological cells in special three-dimensional architectures which are much closer to a physiological architecture.

Spheroids are tightly packed groups of cells with a round shape. They lack any physiological shape. Moreover, should a user wish to work with several cell types in parallel in one object, their only option is to form a spheroid from the desired cell types. However, in this case the shape of the spheroid is undirected and leads to a random distribution of the cells in the spheroid. This process does not make it possible, therefore, to discretely position the cells in relation to one another. This random distribution reduces the meaningfulness of the models, if for example experiments with viruses, bacteria or substances such as pharmaceuticals are to be carried out on them. Since a physiological architecture is not achieved, it is also virtually impossible, for example, to draw direct conclusions regarding the in vivo behavior in the body. Moreover, the body's extracellular matrix (ECM) is also missing. The interaction between ECM and the cell also has a significant influence on the biology of the cell. It is important for the cell to find an environment which corresponds to its usual physiological niche. If this is not the case, it may rapidly lead to cell dedifferentiation, cell death or simply cell stasis. Furthermore, the ECM must resemble in vivo conditions in terms of the physical parameters such as e.g. rigidity or porosity. Finally, the shape itself is a determining factor. The shape of a physiological environment also has an influence on the function. Thus, for example, vascularization must be ensured if supply to larger tissue is to be guaranteed. If, due to lack of vascularization, a tissue can only receive an insufficient supply, it risks dying or losing its function.

The previous possibilities only allow these abovementioned conditions to be reproduced insufficiently, or not at all. In contrast, methods according to the invention offer a possibility of producing complex biological cell architectures. The methods described herein are intended particularly for a user who does not have access to lithographic 3D printing or bioprinting.

SUMMARY OF THE INVENTION

Because of the disadvantages of the methods known in the state of the art for producing cell culture constructs, an object of the present invention is to produce a 3D scaffold colonized with biological cells, by means of which a high degree of similarity to a physiological architecture can be achieved, in order for example to be able to carry out tests with bacteria, viruses or active substances on these tissues. Methods for producing the 3D scaffold colonized with biological cells are also to be provided.

In some designs, the present invention relates to a method for producing a 3D scaffold of a biocompatible polymer being colonized with biological cells, wherein the 3D scaffold has an at least partially covered cavity. In this case, the method according to the invention is divided into the following two steps:
 (a) constructing a 3D scaffold of a biocompatible polymer using a lithographic 3D printing method; and
 (b) filling the at least partially covered cavity with a suspension containing biological cells to colonize the 3D scaffold with biological cells.

EP 3 018 531 A1 describes a 3D printing method which makes it possible to work with multiple bio-inks or cell types in parallel in a printing process. This technology may be used in the present case in order, in the first step, to produce the objects described herein, which can then, in the second step, be colonized with biological cells by a user.

The construction of a 3D scaffold of a biocompatible polymer using a lithographic 3D printing method offers the possibility of printing a biocompatible polymer in a physiological shape, such that material and architecture resemble the structure in the human body to be simulated. Since, according to the invention, the biological cells can only subsequently be introduced into the 3D scaffold for colonization, it is possible to construct a 3D cell culture construct of any cell type.

By the expression "of a biocompatible polymer" it is meant that the 3D scaffold is preferably constructed using a matrix of one or more biocompatible polymers. Although this does not exclude the 3D scaffold containing other constituents aside from biocompatible polymers, it is also possible that the 3D scaffold only consists of biocompatible polymer.

In some designs of a method according to the invention, it is preferred that the 3D scaffold is constructed using a stereolithographic 3D printing method. A stereolithographic 3D printing method here means one in which the structure of the 3D scaffold is produced gradually by curing in layers.

In some designs of a method according to the invention, it is preferred that the 3D scaffold is constructed in step (a) by the following step:
 (i) curing a photopolymerizable or photocrosslinkable substance by focusing an electromagnetic radiation in a focal plane in which the photopolymerizable or photocrosslinkable substance is present.

Preferably, in this case, the photopolymerizable or photocrosslinkable substance is present in liquid form, for example dissolved in a solvent. Hereinafter, reference will be made to a photopolymerizable or photocrosslinkable liquid.

In this case, step (i) is preferably repeated by focusing a further electromagnetic radiation in a further focal plane. When repeating step (i), a further photopolymerizable or photocrosslinkable substance is preferably used.

"Photopolymerizable" here means that the corresponding substance can be polymerized by the action of electromagnetic radiation and optionally the presence of a photoinitiator. "Photocrosslinkable" here likewise means that an oligomer or polymer can be crosslinked by the action of electromagnetic radiation and optionally the presence of a photoinitiator.

In some designs of a method according to the invention, it is preferred that step (a) is divided into the following method steps:

(I) introducing a photopolymerizable or photocrosslinkable liquid into a reaction vessel, (II) focusing an electromagnetic radiation on a focal plane which lies within a region of the reaction vessel filled with the liquid, (III) producing a polymerized or crosslinked structure in a layer of the focal plane in the reaction vessel through the electromagnetic radiation, (IV) introducing a further photopolymerizable or photocrosslinkable liquid into the reaction vessel, with the result that a previously produced polymerized or crosslinked structure is at least partially covered with the further photopolymerizable or photocrosslinkable liquid, (V) focusing a further electromagnetic radiation on a further focal plane which lies within a region of the reaction vessel filled with the further liquid, (VI) producing a further polymerized or crosslinked structure in a further layer in the reaction vessel by the further electromagnetic radiation, wherein the further polymerized or crosslinked structure is arranged directly on the previously produced polymerized or crosslinked structure and is bonded thereto, (VII) repeating steps (IV) to (VI) with a further photopolymerizable or photocrosslinkable liquid in each case, until the 3D scaffold has been produced.

The further focal plane in step (V) preferably differs from the first focal plane at least with respect to the already produced polymerized or crosslinked structure or with respect to the layer of this polymerized or crosslinked structure.

The bonding of the polymerized or crosslinked structures produced in step (VI) is preferably bonding through covalent bonds. However, non-covalent bonds, for example those based on physical interactions, are also possible.

Due to the different focal planes in which a polymerization or crosslinking of the photopolymerizable or photocrosslinkable liquids takes place, a layered construction of the 3D scaffold is consequently achieved. This makes it possible to form the at least partially covered cavity in the 3D scaffold. Furthermore, undercuts and overhanging structures can also be formed, since a polymerization or crosslinking of the photopolymerizable or photocrosslinkable liquid can also take place in a specific focal plane or layer if there is no already polymerized or crosslinked material arranged thereunder but rather only as yet unpolymerized or uncrosslinked liquid. A polymerization or crosslinking of a photopolymerizable or photocrosslinkable liquid present outside the focal plane does not take place; rather, only the photopolymerizable or photocrosslinkable liquid lying within the focal plane is polymerized or crosslinked. Nonetheless, the liquid present outside the focal plane serves to temporarily support the liquid present in the focal plane, without solid support structures being necessary for this purpose.

One or more of the photopolymerizable or photocrosslinkable liquids used can contain biological cells. If a polymerization or crosslinking occurs as a result of the irradiation by the electromagnetic radiation, the cells contained in the liquid will also be embedded in a corresponding polymer. However, it is preferred according to the invention that no biological cells are used in the lithographic 3D printing method.

Methods according to the invention make it possible to produce complex biological 3D cell culture constructs as models in order to represent and investigate, for example, cell-cell interactions, organ biogenesis, diseases or organ functions. Such a 3D cell culture construct has considerable advantages compared to conventional two-dimensional cell culture, in particular regarding modeling the interaction of several cell types. This is because the complexity of cell-cell interactions, the function of a natural barrier and the modeling of diseases or organs cannot be sufficiently reproduced using conventional two-dimensional cell cultures.

Moreover, methods according to the invention make it possible to create miniaturized models particularly simply. Such miniaturized models have hitherto been constructed manually in some cases. The effort required for this is extremely high; in addition, many years of experience are necessary.

Finally, methods according to the invention make it possible to guarantee a high degree of reproducibility of different copies of the same 3D cell culture construct. The use of a 3D scaffold additionally enables the targeted construction of a 3D cell culture. Consequently, not only do methods according to the invention make it possible to accelerate production compared to other methods known from the state of the art, but the 3D cell culture constructs produced also always have the same quality. Such a high degree of reproducibility is particularly advantageous in biotechnology. This is because, when analyzing and developing new pharmaceutical products, testing on constantly consistent three-dimensional cell cultures significantly reduces the development costs. On the contrary, if such complex three-dimensional structures are constructed manually, individual variations are inevitable. This makes it virtually impossible to obtain reproducible test results. In contrast, methods according to the invention provide 3D cell culture constructs which are exceptionally well-suited to producing reproducible test results.

Cavities (so-called wells) of commercially available microtiter plates (for example microtiter plates having 6, 12, 24, 48, 96, 384 or 1536 cavities), cell culture flasks or Petri dishes can be used as reaction vessels in methods according to the invention.

The 3D scaffold produced by means of a method according to the invention can be constructed from a homogeneous material and consequently only comprise a polymer of a single type. In some variants, however, the one photopolymerizable or photocrosslinkable liquid and at least one of the further photopolymerizable or photocrosslinkable liquids are different liquids. This makes it possible to produce heterogeneously constructed 3D scaffolds comprising different polymers. It is possible in this way to achieve different polymer structures within the 3D scaffold. Thus, for example, the at least partially covered cavity can be surrounded by a polymer structure which differs from the polymer structure of the external scaffold of the 3D scaffold, in order for example to have a larger porosity which enables the penetration of the biological cells into the matrix of the 3D scaffold. Furthermore, the at least partially covered cavity can also have columns, a grid or crosspieces in order firstly to support the roof of the cavity and secondly to enable adhesion of the biological cells to the surface within the cavity. The properties of the polymer structure or the various polymer structures within the 3D scaffold can be influenced by the choice of the monomers to be polymerized or the polymers to be crosslinked in the photopolymerizable or photocrosslinkable liquid(s). The lower the molecular weight of the polymerizable or crosslinkable units, generally speaking the smaller the interstices or pores of the resulting matrix of the 3D scaffold are. However, the last-mentioned case is also heavily dependent on the number of crosslinkable units in the polymers and therefore the degree of crosslinking. The higher the degree of crosslinking, generally speaking the smaller the interstices or pores of the resulting matrix of the 3D scaffold are. In principle, the lithographic 3D printing method makes it possible to use different polymer or monomer solutions in each layer in order to obtain a 3D scaffold with a high level of complexity or diversity.

The designation "biocompatible polymer" is used herein to refer to a biological or biologically compatible polymer. "Biologically compatible" as used herein means that it does not influence the lifespan of the biological cells, particularly therefore does not have a toxic effect on the biological cells.

In further designs of a method according to the invention, the 3D scaffold is one which is transparent at least in the visible light range. This makes it possible to optically track and record the colonization with biological cells.

The photopolymerizable or photocrosslinkable substance in the photopolymerizable or photocrosslinkable liquid is preferably one having a photoreactive group which can form covalent bonds with further photoreactive groups.

In some variants, the photoreactive group is an acrylic group, by means of which the polymerization or crosslinking is carried out. That is to say the photopolymerizable or photocrosslinkable substance is preferably an acrylic compound, for example one from the following group: methacrylates, methyl acrylates, ethyl acrylates, hydroxyethyl acrylates, butyl acrylates, trimethylolpropane acrylates, triacryl acrylates and polyacrylates (PA) in general. The substance to be polymerized or crosslinked can be a polymer, an oligomer or a monomer. Preferably, these are carbon-based substances. In the case of monomers, photopolymerization is carried out. In the case of polymers or oligomers, photocrosslinking is preferably carried out.

As monomers to be polymerized, the following can for example be used: acrylamides, vinyl chloride, ethylene, propylene, isoprene, caprolactam, all amino acids, (de)oxyribonucleotides, glucose, and all monosaccharides, as well as the abovementioned acrylates.

As oligomers or polymers, the following can be used: polyethylene glycol (PEG), polyethylene (PE), polypropylene (PP), polyketone (PK), polyvinyl chloride (PVC), polystyrene (PS), polytetrafluoroethylene (PTFE), polymethyl methacrylate (PMMA), polycarbonate (PC), polyethylene terephthalate (PET) and polyurethane (PU). Further, synthetic polymers such as silicones, polydimethylsiloxane (PDMS) or resins such as melamine or melamine-formaldehyde resins are suitable as starting substance. Further, biopolymers such as for instance proteins, DNA, RNA, carbohydrates and carbohydrate derivatives, collagens, fibrins, alginates, gelatins, hyaluronic acids or polylactides are suitable as starting substances. Instead of the abovementioned polymers, it is also possible to use in each case the monomer precursors or oligomer precursors of these polymers as starting substances, as long as these can be stably provided in the solid or liquid state. The introduction of a photoreactive group, for example an acrylic group, into the starting substance makes the latter photopolymerizable or photocrosslinkable. The radiation-induced coupling of the acrylic radicals between various molecules of the starting substance produces a polymerized or crosslinked matrix.

If photopolymerizable PDMS is used as matrix or as enveloping substance, a gas exchange between the cells embedded in this matrix is possible. As already mentioned, different enveloping substances or matrices can be used. Thus, for example, aside from PDMS or another matrix which has good biocompatibility, it is possible to use a stable plastic for the rest of the matrix, in order in this way to produce an outwardly stable object, the interior of which contains a matrix which enables cell growth and has lower stability.

The starting substance supplemented by the photoreactive group is used in a liquid manner, with different viscosities being possible. That is to say, the methods described herein are not restricted to photopolymerizable or photocrosslinkable liquids with a specific viscosity; rather, low-viscosity liquids can also be used. Both Newtonian and non-Newtonian fluids can be used.

The liquids can be solutions or colloidally dispersed mixtures, such as for instance suspensions. In this case, the liquids can have an aqueous to oily character. This is determined inter alia by the choice of the starting substances and the particle sizes thereof.

In order to be able to achieve a photopolymerization or photocrosslinking of the starting substance bearing a photoreactive group, a radical former (what is referred to as a photoinitiator) is also used, which forms radicals at a selected wavelength of the electromagnetic radiation used in the context of the method.

Suitable radical formers are, for example, anthrone derivatives such as for instance violanthrone or isoviolanthrone, fluorescein, rubrene, anthrazine derivatives, tetrazene derivatives, benzanthrone, benzanthronil, eosin, levolinic acid derivatives, phosphine derivatives, mono- and bis-acylphosphines, metallocenes, acetophenones, benzophenones, xanthones, quinones, ketone derivatives, hydroxy ketones, amino ketones, benzoyl peroxides, pyridine salts, phenylglyoxylates and/or iodonium salts.

In addition to the radical former, use is preferably also made of a vinyl macromer and an amine-based co-initiator, in order to enable the photopolymerization or photocrosslinking to proceed in a particularly suitable manner. Ascorbic acid and tertiary amine derivatives, such as for instance methyl diethanolamine or tetraethylamine, are suitable for example as co-initiator.

In some variants, the photopolymerizable or photocrosslinkable liquid has a thiol derivative. Suitable thiol derivatives are dithiothreitol, monofunctional cysteines, bifunctional peptides and similar compounds.

Moreover, a substance can be added to the photopolymerizable or photocrosslinkable liquid which prevents a photopolymerization or photocrosslinking of deeper liquid layers. Thus, liquid solution outside the focal plane remains liquid, even if it is located in the irradiation region of the focal plane lying over it. This functions by absorption of the substance at the wavelength at which the polymerization takes place (polymerizing wavelength). The capture takes place in the focal plane, with the result that it is not possible for the polymerizing wavelength to penetrate into deeper layers. All substances which absorb in the desired wavelength, such as for instance dyes, are suitable.

Moreover, in some variants, it is possible for the one photopolymerizable or photocrosslinkable liquid and/or one of the further photopolymerizable or photocrosslinkable liquids and/or another liquid which does not have to be photopolymerizable to have a temperature-sensitive gelling agent. Provision is particularly made for the use of an inversely temperature-sensitive (also referred to as reverse temperature-sensitive) gelling agent. Such a gelling agent becomes increasingly solid with rising temperature. By heating the reaction vessel, the reaction liquid solidifies and forms a gel which is initially only metastable. If the liquid is not simultaneously photopolymerized or photocrosslinked, the metastable gel can be re-liquefied by subsequent cooling of the 3D scaffold and pumped out. In the case of customary temperature-sensitive gelling agents, the temperature relationships to be applied are exactly the opposite. Thus, for example, as required, a support structure can be created, with the result that hanging structures can be produced. If, on the other hand, the metastable gel is at least partially irradiated with electromagnetic radiation at the suitable wavelength, this leads to a photopolymerization, with the result that the metastable gel in these regions is converted into a stable gel or polymer.

In other words, the temperature-sensitive, particularly inversely temperature-sensitive, gelling agent and the control of the temperature of the reaction space make it possible to work even more simply with hanging parts and undercuts or cavities. In this variant, too, it is possible to also work with liquid structures as support.

Moreover, it is possible to provide a temperature gradient, with the result that a metastable gel does not arise in all regions of the liquid which has the temperature-sensitive, particularly inversely temperature-sensitive, gelling agent added to it. Using such a gradient makes it possible to produce even more complex structures.

The abovementioned individual components can be present as individual substances in the photopolymerizable or photocrosslinkable liquid. Alternatively, it is also possible to produce the substances or groups preferably used for gel formation in a single polymer by corresponding synthesis. Instead of a mixture of individual components, such a polymer would then have different functional groups, which bring together all the functions required, or preferably to be used, for a photopolymerization or photocrosslinking. Further, it is also conceivable to provide just some of the functions or groups preferably used for the photopolymerization or photocrosslinking in one polymer, and to add other functions or groups preferably to be used for the photopolymerization or photocrosslinking in separate individual components of the photopolymerizable or photocrosslinkable liquid.

Alternatively or additionally to the formation of cavities by using a gelling agent, enzymes can also be used to digest the polymer. The principle is as follows: a 3D scaffold with cavities/undercuts (e.g. a channel system) is printed as a solid body, with all the cavities being filled with a sacrificial material during printing, which can be dissolved later (i.e. after conclusion of the printing) by adding the correct enzyme. The sacrificial material is for example a digestible polymer which is digested by adding a digesting enzyme. This is an elegant strategy for creating cavities with stereolithographic printing methods. For example, a hyaluronidase (digesting enzyme) can digest hyaluronic acid (sacrificial material), with the result that a cavity is formed at the location in the 3D scaffold where the hyaluronidase is used. This principle has already been described in the patent application having the official file number DE 10 2019 200 792.9. Alternatively, to create a cavity/undercut, a photoblocker can also be used in the photopolymerizable or photocrosslinkable liquid, wherein the photoblocker restricts the depth of cure of the photopolymerizable or photocrosslinkable liquid.

In some variants, the further photopolymerizable or photocrosslinkable liquid is only introduced into the reaction vessel when the photopolymerizable or photocrosslinkable liquid previously located in the reaction vessel (this can for example be the one photopolymerizable or photocrosslinkable liquid or a further photopolymerizable or photocrosslinkable liquid) has been removed from the reaction vessel. To this end, it is for example possible that a pump is provided which pumps an already used photopolymerizable or photocrosslinkable liquid out of the reaction vessel and pumps a new further photopolymerizable or photocrosslinkable liquid into the reaction vessel. Instead of an individual pump, it is also possible to use two or more different pumps for such processes.

In some variants, the 3D scaffold, during or at the end of the process for producing same in step (a) of a method according to the invention, can be irradiated with electromagnetic radiation of a short wavelength (for example in the UV range, i.e. below 380 nm), in order thereby to achieve a sterilization. Such UV sterilizations are known in principle.

In some variants, a carrier plate or carrier structure to which the first polymerized or crosslinked structure is bonded is arranged in the reaction vessel. The use of such a carrier plate is expedient if the 3D scaffold produced is not to be investigated at a later time in the reaction vessel itself, but rather is to be removed from the reaction vessel. In the carrier plate, screw connections (such as for instance DIN screw connections), for example, can be present in order to enable a subsequent supply of liquids and gases to the 3D scaffold produced. It is also possible to introduce such screw connections into the matrix of the 3D scaffold as part of the production method, i.e. to produce these screw connections there in the matrix. The production of such screw connections in the matrix can be undertaken regardless of whether or not a carrier plate is used.

In some variants, a carrier plate is produced, before the step of producing a first polymerized or crosslinked structure by irradiation with an electromagnetic radiation in a focal plane lying within a region of the reaction vessel filled with a photopolymerizable or photocrosslinkable liquid (in particular with the first or one of the further photopolymerizable or photocrosslinkable liquids), by forming a polymerized or crosslinked carrier structure which has or constitutes the carrier plate. This means that, in these variants, not only the actual polymerized or crosslinked structures, but also the carrier structure, are produced by a polymerization or crosslinking reaction.

The carrier structure can have a shape such that a gap is formed between the carrier plate and a base of the reaction vessel. As a result, the focal planes of the actual polymerization or crosslinking reactions then have a larger gap from the base of the reaction vessel. The first formed polymerized or crosslinked structure then particularly has a larger gap from the base of the reaction vessel. Polymerizable or crosslinkable liquids which are no longer required can then be particularly easily suctioned off from the reaction vessel.

In some variants, an optical system which serves to focus the electromagnetic radiation on the respective focal plane in the reaction vessel is arranged between a source for the electromagnetic radiation (radiation source), which serves to generate the one and/or the further electromagnetic radiation, and the reaction vessel. In this case, in some variants it is provided that a refocusing of this optical system can take place in order to change the focal plane within the reaction vessel. Such a refocusing can be achieved for example by changing the gap between the optical system and the radiation source. In this case, a computer-controlled stepper motor can be provided in order to facilitate a corresponding movement of the optical system. The optical system can for example be a system of optical lenses or—in a construction supported in a particularly simple manner—an individual focusing lens.

In some variants, it is also possible to carry out a relative movement between the reaction vessel or a carrier plate arranged in the reaction vessel on the one hand and the radiation source which serves to generate the one and/or the further light radiation on the other hand. This is because a relative movement of this kind, which can for example be effected by a movement of the reaction vessel, by a movement of the carrier plate arranged in the reaction vessel or by a movement of the radiation source, also makes it possible to change the focal plane within the reaction vessel. As a result, in these variants, no refocusing of an optical system optionally to be used is required. This makes it possible to reduce the risk of optical misalignment.

In further variants, the one and/or the further electromagnetic radiation is directed onto a defined and predeterminable region in the respective focal plane within the one photopolymerizable or photocrosslinkable liquid and/or the further photopolymerizable or photocrosslinkable liquid. That is to say, a specific radiation pattern can be specified which impinges on the photopolymerizable or photocrosslinkable liquid and at these locations serves to polymerize or crosslink the liquid to form a polymer or a gel (the matrix). Such a radiation pattern can for example be produced using masks or collimators, but also using pulsed radiation or by digitally modulating a radiation signal. At the regions of the photopolymerizable or photocrosslinkable liquid impinged upon by the radiation, a polymerization or crosslinking takes place. At the other regions that are not impinged upon by the radiation, however, the photopolymerizable or photocrosslinkable liquid remains in its unpolymerized or uncrosslinked state. Thus, the radiation defines the regions where a printing of the polymerized or crosslinked structure occurs. Such a light-assisted printing makes much higher resolutions possible than is the case in the methods known from the state of the art. In this case, the resolution is dependent on the wavelength of the radiation used. Even at the commonly used long wavelengths, it is better than the resolution which can be achieved with the conventional methods known from the state of the art. The more precisely the radiation source can be focused, the higher the resulting resolution. For example, very high resolutions can be achieved with a laser.

If required, the electromagnetic radiation can be directed onto the respective focal plane via mirrors.

The irradiation pattern selected in each case can be provided for example by a computer program. It is thus conceivable for a user to create the 3D scaffold to be produced by means of a CAD program. The digital object created in such a way is then cut up into individual irradiation planes by a suitable computer program. Further, each plane or different locations in each plane is assigned a specific photopolymerizable or photocrosslinkable liquid. With regard to this information, control information is created for a printer, by means of which the described method is carried out. This control information specifies when and which photopolymerizable or photocrosslinkable liquid has to be introduced into the reaction vessel. Further, this control information specifies when and which image of an irradiation plane is to be projected onto the respective focal plane in the reaction vessel. This makes it possible to then convert the 3D scaffold created beforehand on a computer into a real 3D scaffold.

In some variants, more than one polymerized or crosslinked structure is produced in the same layer (i.e. in the same focal plane). To this end, a polymerization or crosslinking of a first photopolymerizable or photocrosslinkable liquid is first effected. Then, the first photopolymerizable or photocrosslinkable liquid is removed from the reaction vessel and a second photopolymerizable or photocrosslinkable liquid is introduced into the reaction vessel. Now, only those regions within the focal plane in the reaction vessel which were not previously irradiated and where there is consequently not yet any polymerized or crosslinked structure are irradiated. As a result, different matrices can be produced in one and the same layer. Consequently, a plurality of polymerized or crosslinked structures are formed in one and the same layer, thus resulting in a heterogeneous layer. Then, the second photopolymerizable or photocrosslinkable liquid can be removed from the reaction vessel and a further photopolymerizable or photocrosslinkable liquid can be introduced into the reaction vessel. The filling level of this further photopolymerizable or photocrosslinkable liquid can now be brought to a level such that the previously formed layer is completely covered. The focal plane can then be displaced, and a further layer of the 3D scaffold to be produced can be constructed by a corresponding polymerized or crosslinked structure. It is in principle possible in this case for individual layers of the 3D scaffold produced to be homogeneous (comprising a polymerized or crosslinked structure of a single type) and other layers to be heterogeneous (comprising polymerized or crosslinked structures of different types), wherein the number of individual structures per layer is unlimited. In practice, besides a single polymerized or crosslinked structure per layer, heterogeneously composed layers having 2, 3, 4, 5, 6, 7, 8, 9 or 10 polymerized or crosslinked structures have proven to be expedient.

In some variants, at least the first structure of the first layer, but particularly each structure of the first layer, is irradiated with the first radiation from two different directions. In this case, these two different directions are preferably opposite one another. Such an irradiation from two different directions achieves particularly secure anchoring of the first layer to the inner surface of the reaction vessel or to a carrier plate arranged in the reaction vessel. As a result, subsequent secure holding, of the whole 3D scaffold produced, on the reaction vessel or on a carrier plate in the reaction vessel is achieved, as a result of which subsequent investigations on the 3D scaffold can be made easier. Typically, the irradiation is effected from above in the case of a reaction vessel which is open at the top. In these variants, the first layer is then preferably additionally irradiated from below, through the base of the reaction vessel. To this end, the reaction vessel must be manufactured from a material which is permeable to the radiation with the selected wavelength. The subsequent layers arranged above the first layer are then preferably in turn only exposed to light from one direction (namely preferably from above), so that the already formed polymerized or crosslinked structures do not lie between the focal plane of the radiation and a radiation source used for emitting the radiation, and therefore are not shone through again by the radiation before their focal plane.

In some variants, the first electromagnetic radiation and/or the further electromagnetic radiation have a wavelength in the range from 200 nm to 1000 nm (i.e. a wavelength lying between the UV range and the infrared range), more preferably in the range from 350 nm to 800 nm. Such wavelengths make it possible to particularly successfully excite the substances preferably used as radical formers such that radicals are formed, in order to enable a polymerization or crosslinking of starting substances bearing acrylic radicals.

Further suitable wavelengths of the electromagnetic radiation used are in the range from nm to 950 nm, particularly from 250 nm to 850 nm, particularly from 300 nm to 800 nm, particularly from 300 nm to 750 nm, particularly from 300 nm to 700 nm, particularly from 350 nm to 650 nm and quite particularly from 350 nm to 400 nm.

The radiations used for the polymerization or crosslinking can comprise the same wavelength or else different wavelengths from the abovementioned wavelength range, in order to enable a suitable polymerization of the different photopolymerizable or photocrosslinkable liquids. In this case, the individual radiations can be generated using different radiation sources or else using one and the same radiation source. It is also possible to use successively different wavelengths within a layer (and thus within a focal plane) in order to polymerize or crosslink different photopolymerizable or photocrosslinkable liquids in the same layer, if a heterogeneous layer is to be formed from different polymerized or crosslinked structures.

In some variants, the method is carried out such that, during the production of the 3D scaffold, at least one functional element is introduced into the 3D scaffold. The functional element here is selected from the group consisting of membranes, channels, pores, sensors, columns, grids, crosspieces, or electrically conductive carriers and chemotactic preparations. Channels and pores can for example be integrated into the object by specific regions of the polymerized or crosslinked structure formed being left open in a plurality of layers one above the other. Membranes can be formed by introducing lipid molecules into the photopolymerizable or photocrosslinkable liquid.

Moreover, salt bridges can also be introduced within the 3D scaffold by means of the photopolymerization or photocrosslinking. This is particularly readily possible if the photopolymerizable or photocrosslinkable liquid contains salts, i.e. is saliferous. In this way, electrical discharge and enervation of the printed 3D scaffold can subsequently take place.

Via sensors already introduced into the 3D scaffold during the production process, the 3D scaffold produced no longer needs to be subsequently manipulated, but rather can be read out directly via the sensors already introduced. This considerably facilitates subsequent analyses of the 3D scaffold colonized with biological cells. For example, by introducing electrically conductive carriers, such as for instance electrodes, it becomes particularly simple to analyze the electrical potential or the electrical properties of the colonized 3D scaffold during a subsequent investigation of the 3D scaffold formed.

By introducing chemotactic preparations, which in some variants can be introduced in different concentrations in different layers in order thus to produce a gradient, the targeted growth/colonization of biological cells within the 3D scaffold after completion thereof can be made possible. If the chemotactic preparation is an attractant, it exerts positive chemotaxis, with the result that the biological cells in the 3D scaffold will orient themselves toward regions of higher concentration of the attractant. If, however, the chemotactic preparation is a repellent, it exerts negative chemotaxis, with the result that the biological cells in the 3D scaffold will orient themselves toward regions of lower concentration of the repellent or toward regions where the repellent is entirely absent. As a result, a targeted growth/colonization of cells can be achieved within the 3D scaffold.

Preferably, at least one filling level sensor is used in order to always precisely identify the liquid level in the reaction vessel. Using this filling level information, the focal plane in which the next polymerization or crosslinking step is to be carried out can then be determined. The data provided by such a filling level sensor can also serve to automatically adapt the focal plane. The data provided by a filling level sensor can also be used to control a pump which facilitates the flow of the photopolymerizable or photocrosslinkable liquids into the reaction vessel. This makes it possible to always introduce precisely the amount of the photopolymerizable or photocrosslinkable liquids into the reaction vessel which is required for constructing precisely the desired layer. As a result, waste is kept to a minimum. Further, this enables the entire method to be carried out cost-effectively.

As can be seen from the previous description of step (a) of methods according to the invention, the step of 3D printing the 3D scaffold can be carried out entirely automatically, with the result that intervention by a user is not required. This additionally facilitates implementation of the methods.

The duration for which the electromagnetic radiation is irradiated onto the respective focal plane can be adapted to the respective requirements of the photopolymerizable or photocrosslinkable liquids used. That is to say, each material is accorded a time for the curing such as is required and expedient for the desired polymerization or crosslinking.

If a carrier is arranged within the reaction vessel, a negative pressure can arise between a surrounding liquid bed and the already polymerized or crosslinked structures on the carrier when said carrier is raised relative to the reaction vessel. However, a potentially prevailing negative pressure can be relieved by suctioning off the radicals of the photopolymerizable or photocrosslinkable liquid remaining in the reaction vessel for the previous polymerization or crosslinking step and introducing a new photopolymerizable or photocrosslinkable liquid. As a result, the carrier can be moved relative to the reaction vessel without needing to worry about tearing the already polymerized or crosslinked structures of the 3D scaffold off the carrier.

If the 3D scaffold is produced on a carrier plate, this carrier plate can be completely lifted out of the remaining liquid in the reaction vessel after the end of the production process. The 3D scaffold produced can subsequently be removed from the carrier plate by the user.

To produce a 3D scaffold in step (a) of a method according to the invention, it is possible for example to use a 3D printing device, such as is described in EP 3 018 531 A1.

By adding a temperature-sensitive, particularly an inversely temperature-sensitive, substance, the production of hanging objects and cavities in the 3D scaffold can additionally be improved. In this case, for example, a substance such as for instance a poloxamer can be added in a concentration such that the photopolymerizable or photocrosslinkable liquid or a non-photopolymerizable or non-photocrosslinkable liquid also gels, without irradiation, in a desired temperature range.

For example, a method in accordance with the invention can proceed as follows: if gelling is to be achieved at a temperature of approx. 20° C. (for example to be referred to as the "gelling temperature"), a poloxamer is mixed into the photopolymerizable or photocrosslinkable liquid in a concentration such that the liquid gels in this region. Mixtures of a plurality of poloxamers are also possible. If possible, the liquid can first be cooled to a temperature below the gelling point. If a hanging structure is desired within the object, the liquid containing the temperature-sensitive gelling agent can be heated to a temperature which lies above the gelling temperature. The liquid then gels. In parallel thereto, the liquid can also be photopolymerized or photocrosslinked. If a region of the temperature-sensitive liquid is not photopolymerized or photocrosslinked, although the liquid is solid at the increased temperature, it can be re-liquefied at any time when the temperature is lowered to below the gelling temperature. Thus, the temperature-sensitive gelled part can act as a support structure until the end of the printing process. After completion of the printing, the temperature can again be lowered to below the abovementioned gelling temperature of for example 20° C. As a result, the non-polymerized or non-crosslinked temperature-sensitive part of the liquid re-liquefies and can be pumped out. If the gel is liquefied, the support structure is removed and the previously supported part of the printed object, which is now photopolymerized or photocrosslinked, hangs free.

It is furthermore preferred that the 3D scaffold has a filling opening, via which the at least partially covered cavity is accessible. The filling opening is preferably arranged on the upper surface of the 3D scaffold, with the result that the cavity can be filled from above with a suspension containing biological cells (also called cell suspension). Thus, in step (b) of a method according to the invention, it is preferred that the filling with the cell suspension is carried out through a filling opening on the 3D scaffold. The filling opening can for example be present in the form of a filler neck which for example enables the precise attachment of a pipette for the filling with the cell suspension.

Furthermore, it is preferred that the 3D scaffold has one or more outlet openings, which are also spatially connected to the cavity in the interior of the 3D scaffold. If, for example, the cavity is filled with a solution before step (b), this can escape via the outlet openings during filling with the cell suspension. To this end, the outlet opening(s) is (are) preferably arranged spatially below the filling opening, preferably as lateral outlets on the 3D scaffold. The partially covered cavity can, however, also be arranged in the form of a vascular vessel, e.g. in order to supply a biological cell tissue to be arranged in a further cavity with a nutrient solution such as blood.

In some designs of a method according to the invention, it is preferred that the 3D scaffold is dried between step (a) and step (b). This gives the 3D scaffold a more durable form which is better for transporting. After completion of the drying/vitrification, the 3D scaffold can be stored for at least six weeks in a refrigerator, protected from light and moisture. In the process, the 3D scaffold shrinks slightly and becomes harder. Wet storage puts the 3D scaffold at risk of deteriorating more quickly. The drying/vitrification is preferably carried out in a sterile environment. Suitable drying temperatures are in the range from 4° C. to 50° C., more preferably in the range from 15° C. to 25° C. The drying can for example be carried out in a drying cabinet, in a climatic chamber or the like.

All naturally occurring eukaryotic and prokaryotic cells are suitable as biological cells which are used for constructing the 3D scaffold colonized with biological cells. The cells used are preferably eukaryotic cells. All cells and cell types occurring in, or forming, the body of a mammal, in particular a rodent and quite particularly a human, are particularly suitable. In some variants, the biological cells used are omnipotent or pluripotent cells. In this case, in some variants, the invention only relates to the use of such cells which can be obtained without the destruction of human embryos. In addition to naturally occurring cells, cells of non-naturally occurring cell lines can also be used as biological cells. Such artificially generated cell lines enable the custom construction of the 3D cell culture construct to be produced. Not only adherent cells, but also suspension cells, can be used as biological cells. It was hitherto not possible with previous systems to generate 3D cell culture constructs from suspension cells, since these do not grow together on their own. However, if there is a support structure, such as columns or a grid, in the cavity of the 3D scaffold, then it is possible with the 3D scaffold to provide a cell culture construct comprising suspension cells, such as for example a lymph node, on which experiments can then be carried out.

Since methods according to the invention enable a combination of different cell types to form a 3D cell culture construct, it is particularly suitable for producing artificial organs. Such artificial organs can for example be miniaturized model objects of a naturally occurring organ, particularly a naturally occurring organ of a human or an animal, such as for instance a mammal or a rodent. Because different photopolymerizable or photocrosslinkable liquids can be used, different gel types, in which the biological cells are embedded, are also possible. In addition, it is possible to combine plastic polymers and biopolymers, with the result that highly stable structures can be produced, in which the biological cells are embedded. During a single printing process, a plurality of 3D scaffolds, even with different forms, can be produced at the same time.

In order for the user to be able to use the 3D scaffold produced in step (a) of a method according to the invention for step (b), the 3D scaffold—if it has been dried beforehand—is rehydrated. For this, the 3D scaffold is preferably placed in water, a salt solution, a buffer, cell medium or a similar physiologically acceptable liquid, preferably for a period of 60 s to 60 min. Ideally, this treatment is effected in a Petri dish or similar under sterile conditions. As a result, the scaffold regains its original size, strength and nature.

To colonize the scaffold with biological cells, a suspension comprising biological cells (also called cell suspension herein) and a desired solvent is preferably mixed. All solutions compatible with cells can be used as solvent. This comprises all aqueous solutions which ensure cell survival. Usually, substances are used to set a neutral pH (pH 7.4) and an isotonic environment, in order to approximate the fluids in the human body (e.g. blood) with the solutions. The concentration of the biological cells in the solvent is preferably in a range from 100,000 to 300,000,000 cells per milliliter. For the colonization of the 3D scaffold, the cell suspension is preferably introduced into the scaffold via the filling opening. In this case, it is preferred that the total volume of the cell suspension to be filled is at most as large as the volume of the cavity of the 3D scaffold. If the desired cell concentration has been set, the user can flush the volume into the scaffold, for example using a pipette. It is preferred that, when filling with the cell suspension, the 3D scaffold has already been filled with a liquid which can then flow out via optional outlet openings. Ideally, however, the scaffold is removed from the medium used for the rehydration for the filling with the cell suspension.

In further embodiments, the liquid used for colonizing the cavity preferably contains cell spheroids. In further embodiments, the liquid used preferably contains a gelling agent which forms a stable hydrogel after the filling, as a result of which the incorporated cells or cell spheroids are immobilized. Use can be made of enzymatically crosslinking gels (e.g. fibrin), physically crosslinking gels (e.g. collagens) or photopolymerizable or photocrosslinkable liquids as the material basis for the gelling agent.

In further embodiments, the cavity is preferably colonized using a tissue resection or a biopsy (what is referred to as ex vivo culture). In further embodiments, the tissue resection/the biopsy can be held in place with a gel-forming liquid.

When colonizing with biological cells, possible columns, grids or crosspieces in the cavity of the 3D scaffold can act as an anchor or retainer for the biological cells, with the result that—in the case of adherent cells—they can adhere to the 3D scaffold or—in the case of suspension cells—they can be cultured to float freely in the 3D scaffold.

After the 3D scaffold has been filled with the cell suspension, the construct which now contains cells can be cultured further. Depending on the internal construction of the cavity, a new 3D cell culture model can now form. In the case of adherent cells, the biological cells adhere to all available structures and to each other, with the result that a 3D structure in the shape of the cavity of the 3D scaffold is formed. In this way, a 3D cell culture model/construct is formed in a controlled manner. If the 3D scaffold is to be colonized for example with tumor cells, a 3D tumor model is formed. If the model is colonized with suspension cells, such as T cells or B lymphocytes, a lymph node-like model or a diffuse B cell lymphoma is formed. If the cavity or else the pore volume of the matrix of the 3D scaffold has been completely colonized, the cells can leave the 3D scaffold, for example via the optional lateral channels. This makes it possible for example to pinch off small spheroids of cells.

In other words, in methods according to the invention the step of culturing the biological cells can also take place after step (b) to form a 3D cell culture construct. The culturing conditions are dependent on the type of cells used. A person skilled in the art in the field of biology generally knows the ideal culturing conditions for various biological cells. The culture conditions to be determined on the basis of the cell type are temperature, composition of the respective nutrient solution, and nature of the culture vessel. By way of example, mention can be made here of the conditions for human blood vessel cells from the umbilical cord: 37° C. and 5% $CO_2$, minimal medium with glucose, all essential amino acids, vitamins and minerals. Here, the culture is preferably in Petri dishes or cell culture flasks which have been coated for tissue cultures (what are referred to as tissue culture-treated surfaces). Said culture conditions are advantageous for numerous human cells. In the case of vascular cells, the use of growth factors which are added to the minimal medium is additionally necessary.

Subsequently, the 3D cell culture construct can be penetrated by further cells, viruses, bacteria, enzymes or active substances, in order to perform tests on the construct. To this end, on the one hand the filling opening or the lateral channels can be used, but some substances or cells can thus also penetrate the material of the 3D scaffold. In this way, for example, tumor cells can be attacked by CAR-T cells.

In some designs, the present invention also relates to a 3D scaffold colonized with biological cells, which is obtainable by methods according to the invention. All features and designs which are mentioned herein in connection with methods according to the invention also apply—as far as possible—to the 3D scaffold colonized with biological cells according to the invention, and vice versa.

The present invention has the following advantages: scaffolds with undercuts or complex architectures which can be colonized by a user themselves were hitherto not possible. The 3D scaffold itself functions as a hollow body, which hitherto would not have been possible without multi-material stereolithography. The complex architecture which influences the behavior of the cells could not be modeled in this way. The production route according to the invention makes it possible to ensure a high degree of reproducibility and parallelism. Despite a complex architecture, the 3D scaffold can be reproduced accurately to the millimeter. Moreover, the system allows, for the first time, the culturing of suspension cells in a 3D construct or the production of vascular structures. The system does not need to be actively shaken, as is otherwise the case in a conventional shake culture. The cells remain alive in the scaffold. The influence of the system makes it possible to achieve considerably longer culturing times. Thus, the colonized system can be cultured for example over periods of several weeks, with the result that it can be used as a replacement product for animal testing. Culturing periods of several weeks were hitherto not possible for some cell types. Furthermore, the behavior of the cells can be tracked online, since the system is preferably transparent to visible light. Continuous measurement using optical methods is ensured. In summary, the scaffold is novel in terms of its shape, architecture, method of use, and physical parameters.

The 3D scaffold which can be used according to the invention preferably has a flat shape, i.e. is preferably larger in its horizontal dimensions than in the vertical dimension. The 3D scaffold can have any footprint, such as for example circular, oval, rectangular or square, the latter two also having rounded corners. Preferably, the 3D scaffold extends vertically prismatically, i.e. the footprint does not substantially change in the vertical direction. The diameter is preferably in the range from 500 μm to 10 cm; particularly, however, the diameter is guided by the size of the well plates, i.e. is preferably specifically 6.8 mm (96-well), 10.4 mm (48-well), 16.2 mm (24-well) and 34.6 mm (6-well). The height is preferably in the range from 500 μm to 10 cm. If the hollow body is a centrally arranged hollow body, its volume is preferably in the range from 10 μl to 50 ml. If the hollow body is formed in the shape of a vascular vessel (channel), the diameter of the channel is preferably in the range from 1 μm to 5 cm.

These and other advantages and features of the invention will be apparent from the following description of representative embodiments, considered along with the accompanying drawings.

DESCRIPTION OF REPRESENTATIVE EMBODIMENTS

Figure 1:
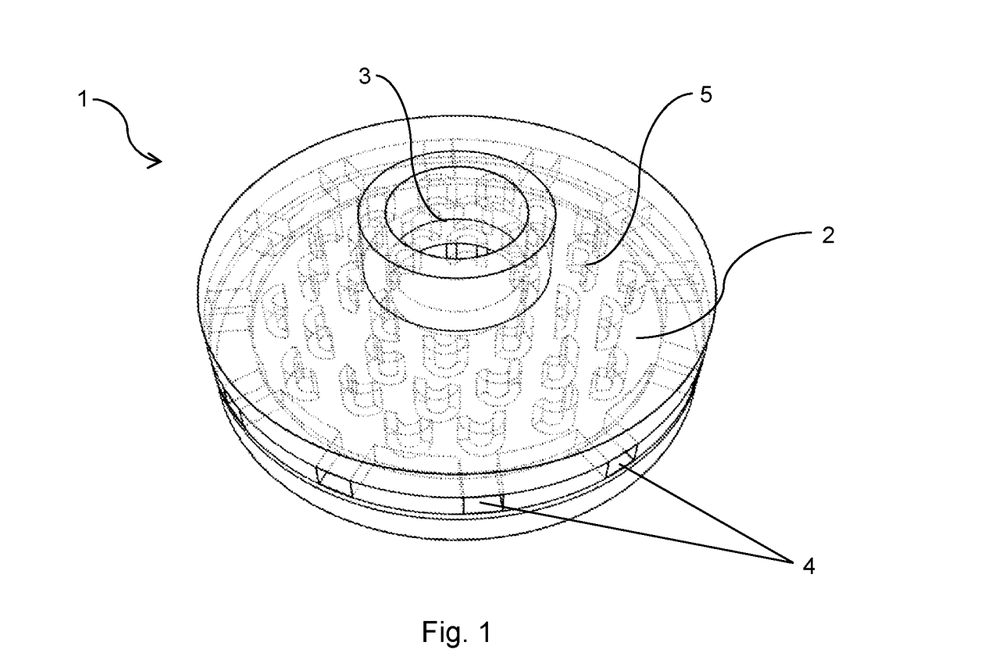
FIG. 1 shows a view of an uncolonized 3D scaffold of a CAD file, having a centrally covered hollow body, a filling opening on the top side and a plurality of lateral outlet openings.

FIG. 1 shows a model of a 3D scaffold 1, created in a CAD file, which can be used according to the invention. The 3D scaffold 1 preferably has a central cavity 2 which is predominantly covered. The cavity 2 is preferably accessible via a filling opening 3 designed as a filler neck. The area above the cavity 2 is preferably supported by columns 5 within the cavity 2. The 3D scaffold 1 preferably has a plurality of lateral outlet openings 4 in the form of outlet channels.

Figure 2:
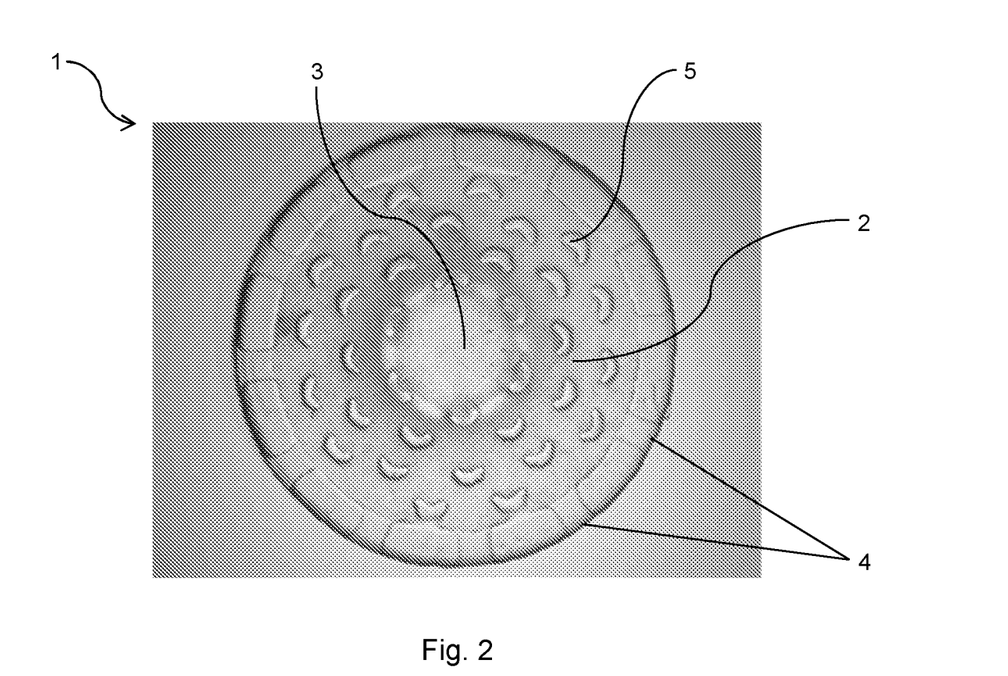
FIG. 2 shows a photograph of a top view of a 3D scaffold produced by lithographic 3D printing according to the CAD file of FIG. 1.

FIG. 2 shows a photograph of a 3D scaffold 1 which has been produced using a lithographic 3D printing method based on the CAD file according to FIG. 1. The top filler neck 3, the lateral channels 4 and the columns 5 in the cavity 2 can be clearly identified. The 3D scaffold shown in FIG. 2 is produced by the following method steps:

1.) creating the CAD file and calculating the master;
2.) equipping the printer with the photopolymerizable or photocrosslinkable liquids to be used;
3.) calibrating the printer, the axes and the printhead;
4.) carrying out the printing; the print platform lowers to the first printing plane for the first photopolymerizable or photocrosslinkable liquid;
5.) printing a first polymer from the first photopolymerizable or photocrosslinkable liquid for architectures consisting of polymer 1 for the first layer height of the construct to be printed; in the process, the calculated construction plan of the first polymer for the first layer height of the construct is projected onto the printing plane in which the printhead is located; here, one or more constructs can be produced simultaneously, depending on the user's wishes and plans; the limiting factor here is the size of the print platform or the installation space;
6.) if necessary, step of washing the printer in order to prevent the first polymer spreading into a second photopolymerizable or photocrosslinkable liquid and vice versa—optional (if a second polymer is required);
7.) if necessary, printing the second polymer for architectures consisting of the second polymer for the first layer—optional (if a second polymer is used);
8.) repeating steps six and seven if a third polymer is used;
9.) changing the printing plane in order to be able to print the second layer height;
10.) printing the first polymer for architectures consisting of the first polymer for the second layer height of the construct to be printed;
11.) if necessary, step of washing the printer in order to prevent the first polymer spreading into the second photopolymerizable or photocrosslinkable liquid and vice versa—optional (if a second polymer is used);
12.) if necessary, printing the second polymer from a second photopolymerizable or photocrosslinkable liquid for architectures consisting of the second polymer for the second layer—optional (if a second polymer is used);
13.) repeating steps 11 and 12 if a third polymer is required;
14.) changing the printing plane in order to be able to print the third layer height;
15.) repeating steps five to eight until the complete architecture has been printed;
16.) after completion of the printing, the print platform is moved into the starting plane and the 3D scaffold obtained is removed;
17.) subsequently, the 3D scaffold can be dried or used immediately;
18.) if the 3D scaffold is dried, this takes place in a sterile atmosphere; here, all water is removed from the 3D scaffold, with the result that a dry polymer scaffold is formed;
19.) after drying, the 3D scaffold can be stored under sterile conditions.

Specific conditions and parameters for the production of the 3D scaffold according to FIG. 2:
- external diameter of 3D scaffold: 6 mm
- height of 3D scaffold: 2 mm
- volume of cavity: 9.9 mm$^3$
- internal diameter of filling opening: 1.6 mm
- cross section of (square) lateral channels and outlet openings: 0.4 mm×0.4 mm
- Composition of First Photocrosslinkable Liquid:
  - solvent: RPMI 1640+25 mM HEPES (Biochrom FG 1383), phosphate-buffered saline
  - photocrosslinkable substance: gelatin methacrylate, 50 g/kg; polyethylene glycol diacrylate, 50 g/l
  - further additives: lithium phenyl-2,4,6-trimethylbenzoylphosphinate, 5 g/kg; tartrazine, 2 mM;

In this example, the entire 3D scaffold is printed from the first photocrosslinkable liquid. Adding the photoblocker tartrazine to the photocrosslinkable liquid regulates the penetration depth of the light used for the polymerization, enabling the production of the covered cavity. Alternatively, for producing the covered cavity, use could be made of sacrificial inks (used in a further photocrosslinkable liquid, e.g. 15 g/kg hyaluronic acid dissolved in RPMI+5 g/kg lithium phenyl-2,4,6-trimethylbenzoylphosphinate, printed and subsequently digested with hyaluronidase in order to produce the cavity), which are dissolved hydrolytically or by enzymatic digestion after completion of the printing.

Figure 3:
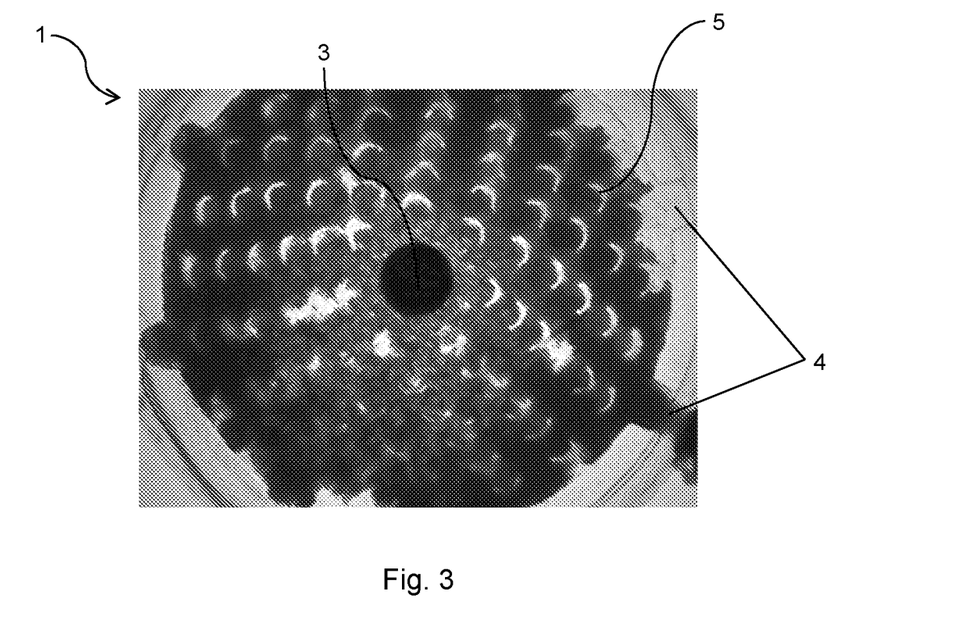
FIG. 3 shows a photograph of a top view of a 3D scaffold according to FIG. 2 colonized with tumor cells from a neuroblastoma.

FIG. 3 shows a photograph of a 3D scaffold 1 according to FIG. 2, which has been colonized with tumor cells from a neuroblastoma. To this end, the following further method steps are carried out:

20.) a cell suspension having a concentration set beforehand by the user is pipetted via the filler neck into a 3D scaffold produced according to 1.) to 19.); in the process, a cell suspension volume is used which corresponds at most to the volume of the cavity of the 3D scaffold; if the 3D scaffold is dried in step 18.), it must first be rehydrated by the user for reuse; a sterile medium such as water, PBS, cell culture medium or the like is suitable for this purpose;
21.) through the pipetting the suspension is distributed within the 3D scaffold and the cells can be cultured within the 3D scaffold;

To colonize the cavity with neuroblastoma cells (SK-N-BE(2)), a cell suspension is produced (solvent: DMEM high glucose+10% FCS+1% penicillin/streptomycin; cell concentration: 150×10$^6$ cells/l). 6 µl of this suspension are pipetted into the cavity of the 3D scaffold via the filler neck. The construct is subsequently cultured at 37° C. and 5% CO$_2$.

Figure 4:
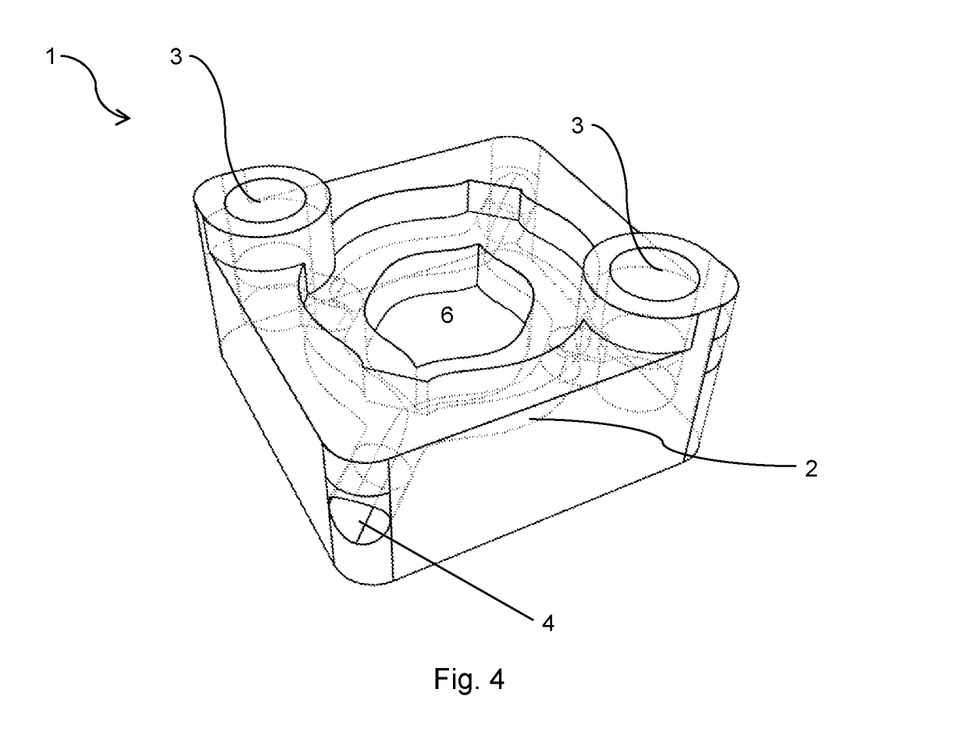
FIG. 4 shows a view of an uncolonized 3D scaffold of a CAD file, having a central recess which is open at the top and also covered cavities in the form of vascular vessels, having two filling openings on the top side for the vascular vessels and two lateral outlet openings of the vascular vessels.

FIG. 4 shows a model of a 3D scaffold 1, created in a CAD file, which can be used according to the invention. The 3D scaffold 1 has a central recess which is open at the top as a colonization region 6 for biological cells. Furthermore, it has cavities 2 which are closed at the top, i.e. covered, in the form of vascular vessels which preferably extend in the horizontal plane around the central colonization region 6. The 3D scaffold 1 shown in FIG. 4 further includes a plurality of lateral outlet openings 4 in the form of outlet channels.

Figure 5:
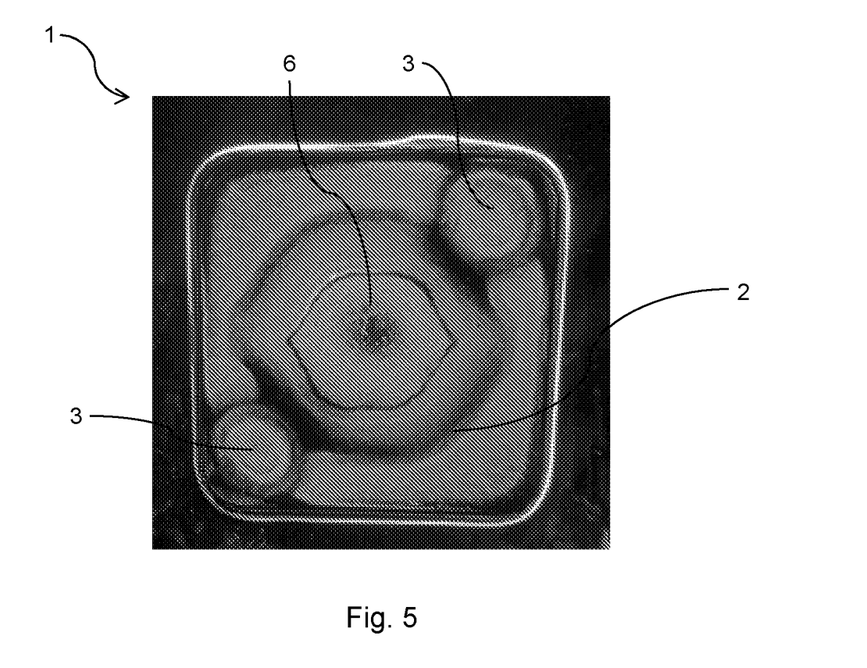
FIG. 5 shows a micrograph of a printed model according to the CAD file according to FIG. 4, from below.

FIG. 5 shows an actually printed 3D scaffold 1 under the microscope, from the underside thereof. Filler neck 3, cavities 2 in the form of vascular vessels and colonization region 6 can be clearly identified.

As used herein, whether in the above description or the following claims, the terms "comprising," "including," "carrying," "having," "containing," "involving," and the like are to be understood to be open-ended, that is, to mean including but not limited to.

The above-described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

LIST OF REFERENCE NUMBERS 1 3D scaffold
2 cavity
3 filling opening
4 outlet opening
5 columns
6 colonization region

The invention claimed is:

1. A method including:
   (a) constructing a 3D scaffold comprising a biocompatible polymer using a lithographic 3D printing method, the 3D scaffold having an at least partially covered cavity and wherein the biocompatible polymer is obtained by rendering a biopolymer as a starting substance photopolymerizable or photocrosslinkable by introducing a photoreactive group, the biopolymer being selected from a group consisting of proteins, DNA, RNA, carbohydrates, carbohydrate derivatives, collagens, fibrins, alginates, gelatins, and hyaluronic acids; and
   (b) filling the at least partially covered cavity with a suspension containing biological cells to colonize the 3D scaffold.

2. The method of claim 1 wherein the 3D scaffold is constructed using a stereolithographic 3D printing method.

3. The method of claim 1 wherein constructing the 3D scaffold includes curing a first photopolymerizable or photocrosslinkable substance by focusing electromagnetic radiation in a first focal plane in which the first photopolymerizable or photocrosslinkable substance is present.

4. The method of claim 3 wherein constructing the 3D scaffold includes curing a second photopolymerizable or photocrosslinkable substance by focusing electromagnetic radiation in a second focal plane in which the second photopolymerizable or photocrosslinkable substance is present, the second focal plane being different from the first focal plane.

5. The method of claim 4 wherein the second photopolymerizable or photocrosslinkable substance is different from the first photopolymerizable or photocrosslinkable substance.

6. The method of claim 1 wherein filling the at least partially covered cavity with the suspension containing biological cells includes directing the suspension containing biological cells through a filling opening on the 3D scaffold.

7. The method of claim 1 further including drying the 3D scaffold prior to filling the at least partially covered cavity with the suspension containing biological cells.

8. The method of claim 1 further including, after filling the at least partially covered cavity with the suspension containing biological cells, culturing the biological cells to form a 3D cell culture construct.

9. The method of claim 8 wherein the 3D cell culture construct is penetrated by further cells, viruses, bacteria, enzymes or active substances.

10. A 3D scaffold comprising:
    (a) multiple layers of a biocompatible polymer, the multiple layers of the biocompatible polymer formed by a lithographic 3D printing method and defining an at least partially covered cavity and wherein the biocompatible polymer is obtained by rendering a biopolymer as a starting substance photopolymerizable or photocrosslinkable by introducing a photoreactive group, the biopolymer being selected from a group consisting of proteins, DNA, RNA, carbohydrates, carbohydrate derivatives, collagens, fibrins, alginates, gelatins, and hyaluronic acids; and
    (b) a suspension containing biological cells filling the at least partially covered cavity to colonize the 3D scaffold.

11. The 3D scaffold of claim 10 further including one or more outlet openings.

12. The 3D scaffold of claim 10 further including columns, grids, or crosspieces in the at least partially covered cavity.

13. The 3D scaffold of claim 10 wherein at least a portion of a first one of the multiple layers of the biocompatible polymer comprises a first photopolymerizable or photocrosslinkable substance cured by focusing electromagnetic radiation in a first focal plane in which the first photopolymerizable or photocrosslinkable substance is present.

14. The 3D scaffold of claim 13 wherein at least a portion of the first one of the multiple layers of the biocompatible polymer or a second one of the multiple layers of the biocompatible polymer comprises a second photopolymerizable or photocrosslinkable substance cured by focusing electromagnetic radiation in a second focal plane in which the second photopolymerizable or photocrosslinkable substance is present, the second focal plane being different from the first focal plane.

15. The 3D scaffold of claim 14 wherein the second photopolymerizable or photocrosslinkable substance is different from the first photopolymerizable or photocrosslinkable substance.

16. The 3D scaffold of claim 10 wherein the biological cells are cultured to form a 3D cell culture construct.

17. The 3D scaffold of claim 16 wherein the 3D cell culture construct is penetrated by further cells, viruses, bacteria, enzymes or active substances.

* * * * *